United States Patent
Brink et al.

(10) Patent No.: US 7,783,357 B2
(45) Date of Patent: Aug. 24, 2010

(54) DUAL BATTERY ARRANGEMENT FOR AN AUTOMATED EXTERNAL DEFIBRILLATOR

(75) Inventors: Gregory Brink, Bainbridge Island, WA (US); Daniel J. Powers, Issaquah, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 636 days.

(21) Appl. No.: 11/815,127

(22) PCT Filed: Nov. 21, 2005

(86) PCT No.: PCT/IB2005/053852

§ 371 (c)(1),
(2), (4) Date: Aug. 7, 2007

(87) PCT Pub. No.: WO2006/061725

PCT Pub. Date: Jun. 15, 2006

(65) Prior Publication Data

US 2008/0208272 A1     Aug. 28, 2008

Related U.S. Application Data

(60) Provisional application No. 60/634,701, filed on Dec. 8, 2004, provisional application No. 60/650,873, filed on Feb. 7, 2005.

(51) Int. Cl.
*A61N 1/378* (2006.01)
(52) U.S. Cl. ........................................... 607/34
(58) Field of Classification Search ............ 607/34
See application file for complete search history.

(56) References Cited

U.S. PATENT DOCUMENTS 4,114,082 A    9/1978 Scheidler (Continued)

FOREIGN PATENT DOCUMENTS

EP    1205215 A    5/2002

(Continued)

OTHER PUBLICATIONS

Patent Abstracts of Japan, vol. 1999, No. 09, Jul. 30, 1999.

(Continued)

*Primary Examiner*—Carl H Layno
*Assistant Examiner*—Yun Haeng Lee
(74) *Attorney, Agent, or Firm*—W. Brinton Yorks, Jr.

(57) ABSTRACT

A defibrillator, equipped with a battery power source, is described which is arranged to operate in any one of both a first mode and a second mode, the battery power source comprising at least two voltage sources. The voltage sources are arranged to be connected in parallel to each other when the defibrillator is operating in a first mode, and in series with each other when the defibrillator is operating in a second mode. The invention can be implemented by a battery pack for a defibrillator. This arrangement allows both voltage sources to be drawn down at the same rate which lengthens the overall life of the batteries. A more efficient use of battery power is thereby obtained. The invention ultimately extends the projected life of the batteries and when applied to an automatic external defibrillator increases the shelf life of the defibrillator.

13 Claims, 5 Drawing Sheets

U.S. PATENT DOCUMENTS

| | | |
|---|---|---|
| 5,121,046 A | 6/1992 | McCullough et al. |
| 6,038,473 A | 3/2000 | Olson et al. |
| 6,549,807 B1 | 4/2003 | Kroll |
| 2006/0111752 A1* | 5/2006 | Greatbatch et al. ............ 607/34 |

FOREIGN PATENT DOCUMENTS

| | | | |
|---|---|---|---|
| JP | 11119843 A | 7/1999 |
| JP | 2004215449 A | 7/2004 |

OTHER PUBLICATIONS

Patent Abstracts of Japan, vol. 2003, No. 12, Dec. 5, 2003.

* cited by examiner

FIG. 6

DUAL BATTERY ARRANGEMENT FOR AN AUTOMATED EXTERNAL DEFIBRILLATOR

This application claims the benefit of Provisional U.S. patent application Ser. No. 60/634,701, filed Dec. 8, 2004 and Provisional U.S. patent application Ser. No. 60/650,873, filed Feb. 7, 2005.

This invention relates to a defibrillator and, in particular, to an automatic external defibrillator (AED) equipped with a battery power source for the purposes of operation.

Sudden cardiac death is a leading cause of death in the developed world. Most sudden cardiac death is caused by ventricular fibrillation, in which the muscle fibers of the heart, which normally contract in a coordinated manner to pump blood around the arterial system of the body, contract instead in an uncoordinated manner. This interrupts what should be the normal flow of blood to the body. The heart, once in ventricular fibrillation, can be forced back into a normal heart rhythm by the application of an electric shock. The application of this shock, known as defibrillation, clears the heart of the abnormal electrical activity by depolarizing a critical mass of myocardial cells to allow normal spontaneous organized myocardial depolarization to resume. Studies have shown that for this to be effective, the defibrillation shock must be delivered to the patient within minutes of the onset of ventricular fibrillation. The commonly used means to apply this electrical defibrillation shock is a defibrillator. A defibrillator applies the electric shock through two electrodes placed on the chest of the victim.

Defibrillators are known in the art and generally comprise an electrode arrangement connected to a charging means which provides a sufficient potential difference between the electrodes to ensure that a current sufficient to restart the heart flows between the two electrodes.

Originally defibrillators were available for use only where mains power was provided, for example in a hospital setting. The more recent development of battery powered defibrillators allowed an extension of their use to areas away from mains power, for example in ambulances or in the open air.

U.S. Pat. No. 6,038,473 describes a defibrillator which is battery powered and which contains an arrangement of three batteries, these being an upper set of batteries in series with a lower set of batteries and a second set of batteries arranged in parallel with one of the upper or lower sets. The upper and lower set of batteries is used together to charge a capacitor bank. The second set cannot be used to charge the capacitor bank and instead is used to provide power to the microprocessor and control circuits. The arrangement increases the life of the second battery arrangement and ensures that the power to the microprocessor is not lost before the power to the capacitors is lost. In other words, the system is designed so that the battery charging the capacitor bank is drained before the battery powering the microprocessor. This uses up the power in the batteries inefficiently and results in power to the capacitor banks being lost early.

It is an object of the invention to provide a defibrillator which is more efficient. This is achieved according to an object of the invention whereby the defibrillator is arranged to operate in any one of both a first mode and a second mode, the battery power source comprises at least two voltage sources, the voltage sources are arranged to be connected in a first sequence when the defibrillator is operating in first mode, and the voltage sources are arranged to be connected in a second sequence when the defibrillator is operating in second mode.

The invention also relates to a battery pack for supplying a first voltage and a second voltage to a defibrillator and comprising at least two voltage sources, in that the voltage sources are arranged to be connected in a first sequence to supply the first voltage, and in that the voltage sources are arranged to be connected in a second sequence to supply the second voltage.

These and other aspects of the present invention will be explained with the aid of the following drawings.

The battery arrangement of a defibrillator in an illustrated embodiment of the present invention comprises at least two individual batteries or battery compositions which may be connected in parallel or in series. Each individual battery composition is itself a string of individual batteries connected in series. When the batteries are connected in parallel they produce an electromotive force, or e.m.f., equal to the e.m.f. of each individual battery or battery composition, depending on which is used. Diodes can be connected in series with each individual battery or battery composition to ensure that they do not attempt to charge each other in the event that they provide unequal voltages. It has been found that the invention works advantageously when the e.m.f.'s of the batteries or battery compositions are equal.

When the individual batteries or battery compositions are connected in series they provide together an e.m.f. equal to the sum of all their individual voltages.

When the batteries or battery compositions are connected in parallel they provide a lower potential difference than when they are connected in series, but are then capable of sustaining greater current flow. This allows the overall battery arrangement to provide different voltages to enable power to be provided to different components in the defibrillator.

In the simplest arrangement there are only two individual batteries or battery compositions and the variation between series and parallel connection produces two separate output voltages.

This arrangement allows both batteries to be drawn down at the same rate and this therefore lengthens the overall life of all batteries in the arrangement. This then achieves a more efficient use of battery power. The invention ultimately extends the projected life of all the batteries in the overall parallel and series arrangement.

The provision by which the individual battery arrangements are arranged to be in parallel or in series may comprise a switch.

Although the simplest arrangement comprises only two individual batteries or battery compositions, the invention can in fact be worked using any number of battery formations and thus can be extended to the use of more batteries. So for example, three individual batteries can be arranged to be either in series or in parallel, or as an alternative example, four or more battery compositions can be used. The choice depends entirely on what voltage sources are available and what the power requirements are to be provided by the invention.

Using three or more batteries or battery compositions in an embodiment of the invention can provide up to three or more distinct voltages. In an illustrated embodiment three batteries are arranged to provide two separate voltages, there being one larger voltage when all battery arrangements are connected in series and one lower voltage when all battery arrangements are connected in parallel. Use of the invention is particularly advantageous when the difference between the required voltages is large. So for example three batteries of 4V can be combined using the principles of the invention to provide an output of only 4V but also an output of 12V.

Using three or more batteries or battery compositions requires greater switching complexity and it has been found experimentally that a formation of just two batteries or battery compositions provides the advantages described without added complexity.

Alteration of the battery formation between connection in parallel and connection in series can be easily effected using any switching arrangement. A MOSFET has been found in practice to be a particularly advantageous switching device to use, but in principle it is possible to use any switching device which may be incorporated into the arrangement. So for example a manual switch may be used in a particularly simple defibrillator arrangement without detracting from the essential elements of the invention.

The invention can be further explained using the example of an automatic external defibrillator, or AED. AEDs are automatic, or semi-automatic, portable external defibrillators which have been developed to be used outside the hospital environment at the scene of a sudden cardiac arrest. AEDs are therefore usually battery powered for portability. This portability has extended their use even further and AEDs are now deployed in environments where defibrillator usage was previously unknown, such as in public shopping and entertainment areas, airports, and other areas where large numbers of people are present. The development of automatic functionality in the AED allows untrained personnel to use them and this has allowed a further extension of their application away from the normal medical environment. It is now possible to provide an AED in a non medical location purely as a precaution in case of a cardiac emergency and with the intention that in the event of its use as a piece of emergency equipment it will be used by someone who is medically untrained. The usage of such AEDs is therefore likely to be infrequent.

This development has required that AEDs be capable of idling, or remaining in a stand-by state, for long periods of time, frequently months and possibly years, without being used, but always with the necessity that they still be in full working order when they are needed. This requirement has imposed constraints on the battery arrangement. The battery arrangement used must provide sufficient power for full operation when needed but allow the AED to rest for long periods of time in-between such periods of use.

The requirement that the AED be capable of automatic use imposes additional functionality. So for example as well as performing the usual functions of charging a capacitor and delivering a shock, the AED also runs self-tests, registers activation, measures impedance between the electrodes, performs analysis on the impedance results, provides the user with simple-to-follow instructions, runs a clock, measures the ambient temperature as well as, of course, charging and discharging the electrodes during use. These added functionalities within the AED may vary between individual designs as is well known in the art.

The various stages of AED operation and self-operation, as is also known in the art, can be thought of as being operation in different modes. So, for example, when the capacitors are being charged the defibrillator may be said to be in charging mode, and when the capacitors are being discharged through a patient to deliver a shock the defibrillator can be said to be in discharge mode. Similarly, the defibrillator may be configured to operate self-tests, although as is currently known in the art, this is not strictly necessary. When and as self-tests are performed the defibrillator may be said to be in self-test mode. When the AED is in operation it may be said to be in run-time mode which comprises capacitor charging and discharge, patient monitoring and analysis, and can also be considered to include self-testing. When not in run-time mode it can be thought to be in stand-by mode comprising running a clock, monitoring environmental conditions, and providing status outputs. These different modes have different current and voltage requirements and it is these different requirements that the invention is able to address. The variable output voltages as provided by the invention are used within the defibrillator to power the various different functions required for the various operations of the defibrillator and do so with significant battery efficiency.

These different modes in which the AED can operate can be used to illustrate battery power management in an AED. During periods of inactivity when the AED is typically in a stand-by mode there is minimal power consumption. In this state efficient power consumption can be assisted through the use of low voltage circuits. In stand-by mode, the AED may maintain a clock or monitor environmental conditions, either or both of which might be used to wake up the AED for periodic or conditional self-testing. During self-testing and during user operation, in other words during use of the AED to rescue a cardiac arrest victim, AEDs operate in run-time mode which is characterized by high power consumption. This high power consumption is required for monitoring patient conditions, analyzing heart rhythms and for operating the high voltage defibrillation circuitry. Optimal performance in run-time mode is realized through the use of higher voltage, higher current circuits. It is very difficult to design a battery power supply which is optimal for both modes of operation and the result is almost always a trade-off between the often conflicting requirements. The present invention allows the provision of different voltages from the battery arrangement described and these voltages can then be used to power different functions.

In order to explain this further, the various modes can be simplified for purposes of illustration into a stand-by mode and a run-time mode.

In stand-by mode, which can be operated by a stand-by circuit, a clock is run to schedule and activate automatic self-tests. In addition, status indicators are operated, such as LEDs, LCDs, or audio beepers, or indeed some combination thereof. The stand-by circuits can also control the activation of the self-test and user modes.

Because the AED is designed as an emergency piece of apparatus to be used by non-expert persons, the AED is generally expected to be in stand-by mode the vast majority of its lifetime. This mode is extremely low power and draws only about 15 μA. It is during this mode that the invention would provide a lower voltage which is more appropriate for the low power requirements of stand-by.

Periodically, the AED turns on its internal systems and runs them through automatic testing. It is now operating in the higher power run-time mode, albeit in a form which can be termed self-test mode. During this time, the AED may for example generate and analyze ECG-like signals, charge and discharge the high voltage capacitor, test battery health and check the electrode impedance. Different subsets of these self-tests are performed for a few minutes on a daily, weekly, and monthly basis.

Another form of run-time mode is user mode, which is activated when a user turns on the AED to perform a cardiac rescue. It is possible for the same systems tested during the self-test mode to be activated during user mode. Both self-test mode and user mode will run at a current greater than 200 mA and it has been found that the current may be significantly higher than 200 mA during charging of the high voltage capacitor. Generally, both run-time and self-test modes require a higher power than is required during stand-by mode. This higher power requirement can be met by a battery arrangement in accordance with the present invention.

An embodiment of the present invention can provide the advantage of a longer battery shelf life. Drawing down the batteries at the same rate provides maximum battery life for a given set of battery cells and ensures that all the cells reach the same minimum voltage at the same time regardless of the operating mode used. This is important in extending the shelf life of the AED between battery changes. Use of the AED to perform an emergency rescue may drain, or nearly drain, the batteries. After use, therefore, it is prudent to check the batteries, or battery pack, of the AED for remaining power. However, the extension of the battery life due to the invention means that the AED can rest unused for longer periods of time before the batteries or battery pack requires replacement, even in the case when the AED has not been used to perform a rescue.

A further advantage of the invention can be described as follows. In the battery arrangement of the prior art, U.S. Pat. No. 6,038,473, the battery arrangement is suboptimal because at least one set of batteries always retains energy that is inaccessible to the defibrillation circuitry. This shortens overall battery life and reduces the number of shocks available to the patient. In a battery arrangement of the invention, each battery cell can be discharged at the same rate, regardless of the operating mode history of the defibrillator. This maximizes battery life and all battery cells will reach their end of life at exactly the same time regardless of operating history and therefore will expend all of the energy in the batteries. The battery arrangement of the invention can thus be seen to extend battery life.

There are a number of other prior art defibrillator battery arrangements. The simplest is an array of battery cells producing a single voltage output to provide for all AED requirements. This arrangement is suboptimal because the voltage that is high enough to be adequate for prompt operation is inefficient for the voltages needed when the AED is resting in stand-by. Ultimately this shortens the battery life to below that of optimum.

The higher power requirement of the run-time and self-test modes has traditionally determined the size of the battery or battery pack used to power the AED, while the requirements of stand-by mode, on the other hand, have necessitated a much lower source of voltage. This discrepancy has resulted in the inefficient use of the applied high voltage power source. This has been particularly true in the instances when linear regulators have been used to develop the voltage needed by the AED in stand-by mode. This inefficient use shortens battery life and thereby reduces the shelf life of the automatic external defibrillator.

Alternatively, one prior art defibrillator comprises two separate batteries of different voltages, one a low voltage battery for stand-by operations, and the other a higher voltage battery for run-time operations. This arrangement requires more maintenance. Two batteries must be periodically replaced in the AED instead of one and must be replaced in the correct positions. If both batteries are provided in a battery pack, which avoids the untrained user having to find the correct insertion point and orientation for each of the two batteries, then the battery pack will have to be replaced whenever one of the two batteries has run down. This will mean that one of the two batteries will be replaced too early. This is inefficient.

The drive to create an automatic functionality in AEDs so that they may be used by untrained personnel has also necessitated that the care and safe use of the AED be as simple as possible. Therefore it is advantageous to provide batteries for an AED in the form of a battery pack which can be plugged into and unplugged from the AED. This reduces the number of components that the untrained user has to be concerned with at any one time. The battery pack of the invention is suitable for providing the arrangement of the invention to the AED when such battery packs are used.

Figure 1:
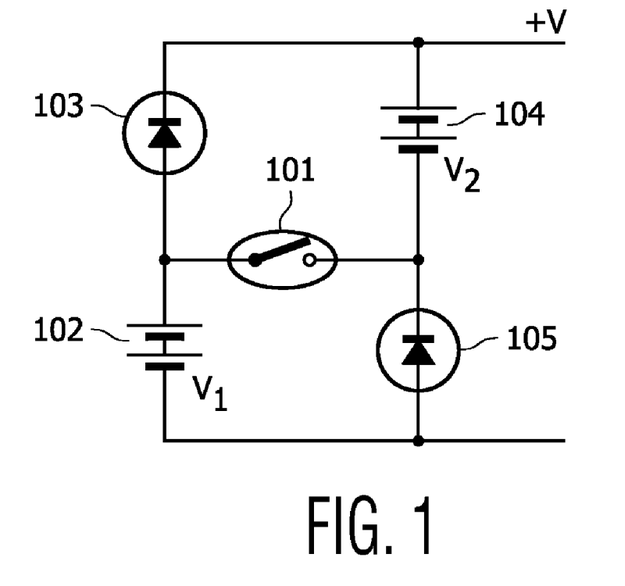
FIG. 1 shows an arrangement of two batteries according to the invention.

Turning now to the drawings, FIG. 1 shows a first embodiment of the present invention comprising an arrangement of two batteries 102 and 104, both of which in this case are themselves made up of two further battery cells. In other words, each is a battery composition instead of a single battery. This concatenation of single batteries is purely optional and depends on the actual power requirements of the defibrillator versus the basic battery units available. The arrangement shows the batteries 102 and 104 connected in parallel and capable of supplying a voltage equal to the voltage of each when the switch 101 is open. Diodes 103 and 105 are shown in series with each battery to stop either battery from trying to charge up the other. Alternatively, switches (not shown) may be substituted for diodes 103 and 105, with switch positions maintained opposite to the switch 101 position.

Figure 2:
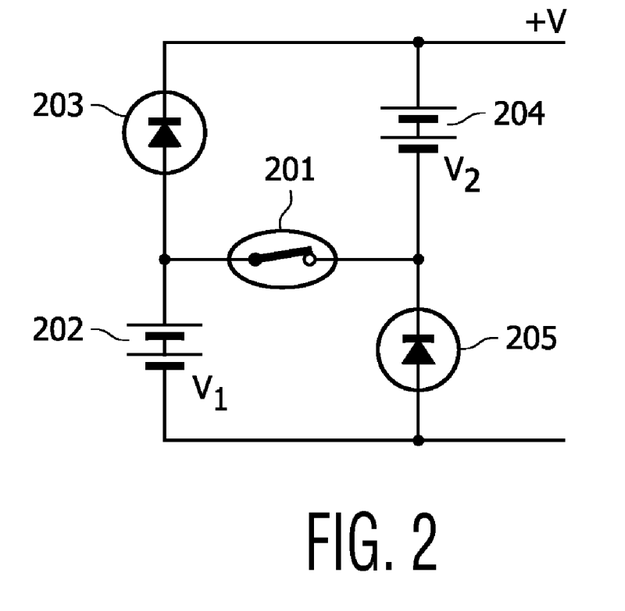
FIG. 2 shows the alternative arrangement of the two batteries provided by the invention.

FIG. 2 shows a second arrangement of two batteries 202 and 204. Here, the switch 201 is closed thereby allowing the batteries to be connected in series and thereby allowing them to be capable of supplying a voltage equal to the sum of the voltages V1 and V2. Diodes 203 and 205 are again shown. Alternatively, switches (not shown) may be substituted for diodes 203 and 205, with switch positions maintained opposite to the switch 201 position.

Figure 3A:
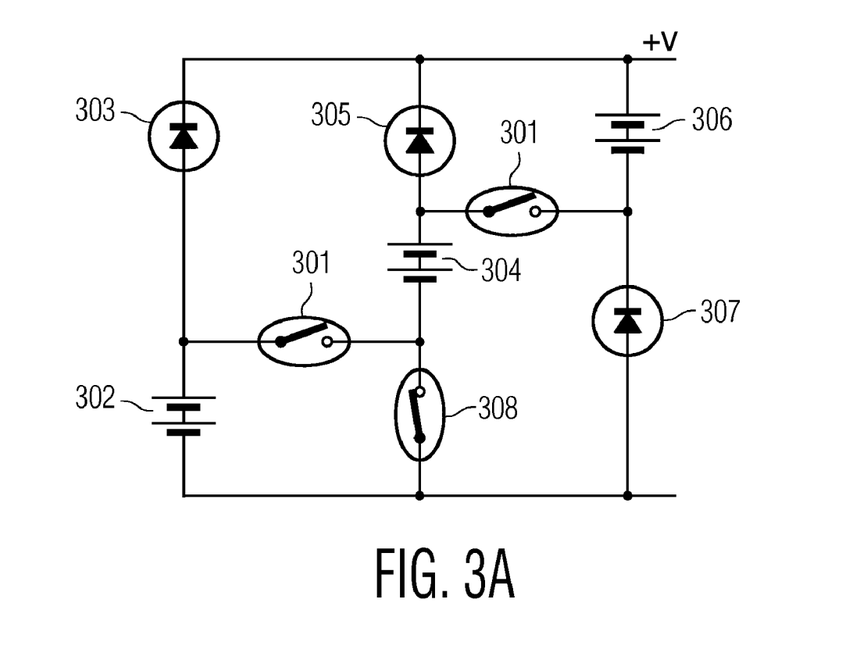
FIGS. 3A and 3B show two arrangements of the invention applied to three batteries.

FIG. 3A shows an embodiment of the invention including an arrangement of three batteries 302, 304 and 306. Two switches 301 and a third switch 308 allow the batteries 302, 304 and 306 to be arranged either in series or in parallel. In this embodiment, the position of switch 308 is always opposite the position of switches 301.

Figure 3B:
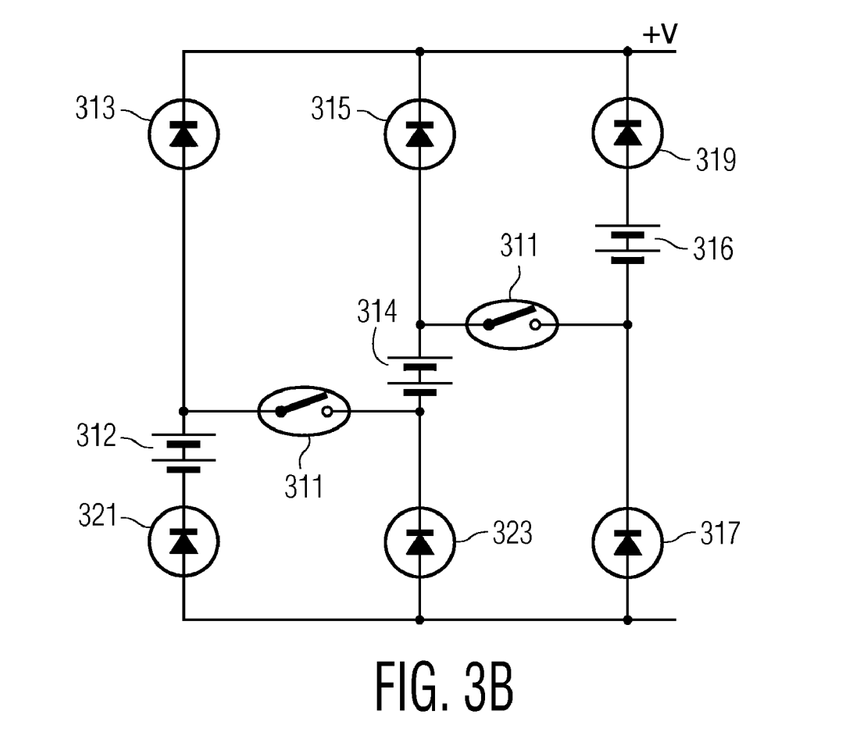

FIG. 3B shows an alternate embodiment of the invention including an arrangement of three batteries 312, 314, and 316. Two switches 311 and six diodes 313, 315, 317, 319, 321 and 323 are arranged to allow the batteries 312, 314, and 316 to be arranged either in series or in parallel depending on switches 311 positions.

Figure 4:
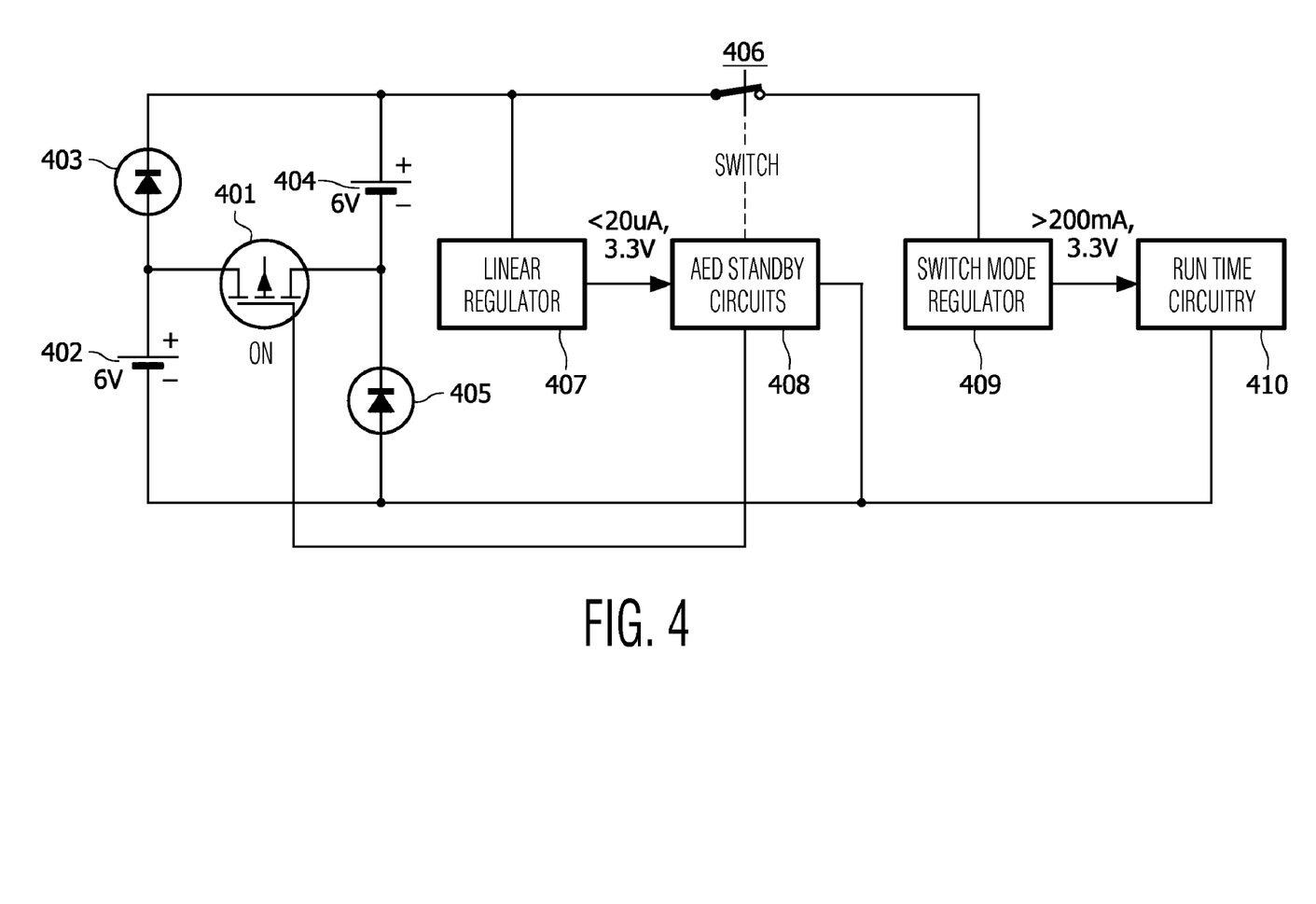
FIG. 4 shows the invention applied in an AED circuit.

FIG. 4 shows how an embodiment of the invention might be applied to the control circuits of an AED. Two batteries 402 and 404 are shown in arrangement with a switch 401 and, in this case, two diodes 403 and 405. The battery arrangement powers the circuitry for the AED which is shown as comprising AED Stand-by Circuits 408 and Run-Time Circuitry 410. The voltage supply to both these sections of circuitry is regulated by, in the case of the AED Stand-by Circuits 408, a Linear Regulator 407 and, in the case of the Run-time Circuitry 410, a Switch Mode Regulator, 409. The properties of both types of regulator are known to those skilled in the art.

Figure 5:
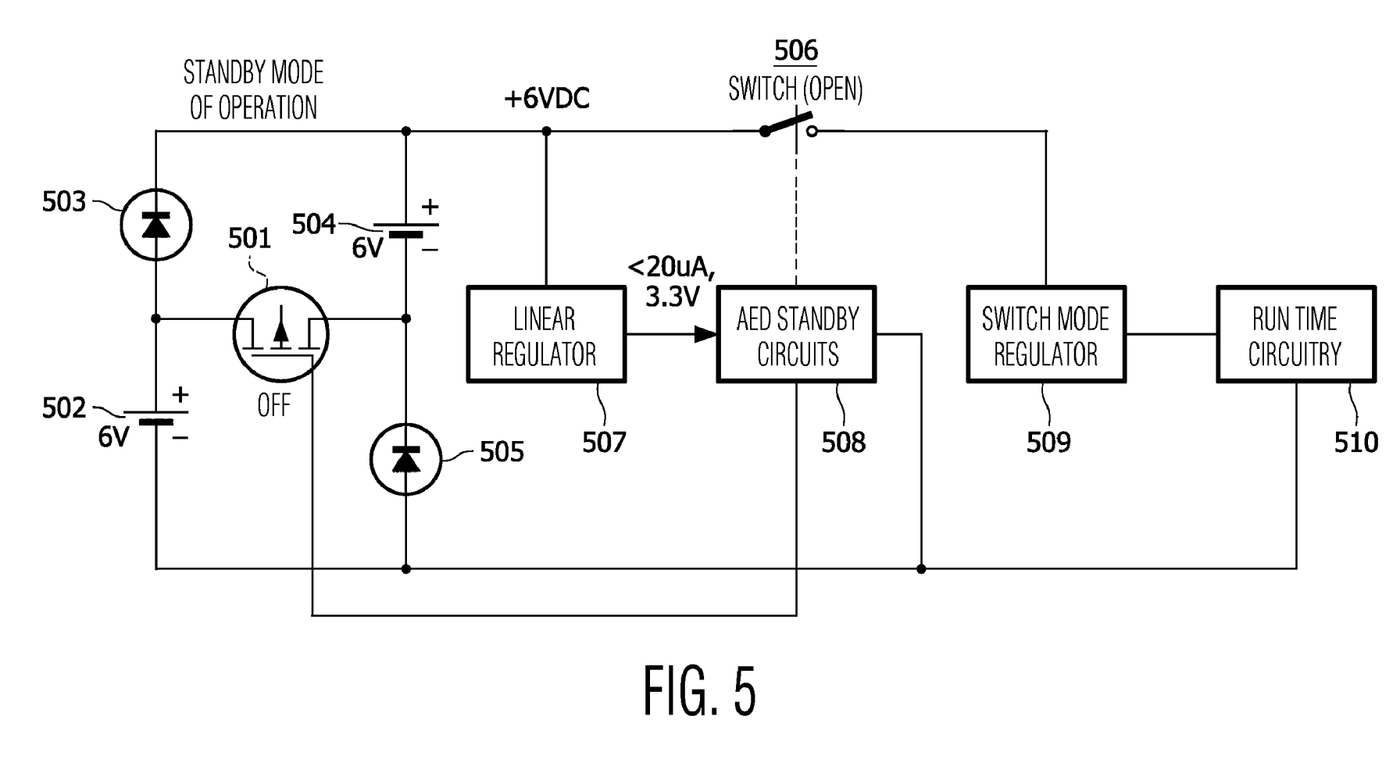
FIG. 5 shows the circuit when the AED is operating in stand by mode.

FIG. 5 shows the circuit of FIG. 4 when the AED is operating in stand by mode. Here switch 501 is open, allowing batteries 502 and 504, both of 6V, to operate in parallel, protected in this case by the existence of diodes 503 and 504. The batteries generate the lower voltage of 6V. Switch 506 is also open and the generated voltage is applied to the linear regulator 507 which operates efficiently at the lower voltage. No power is supplied to the Switch Mode Regulator 509 and the Run-time Circuitry 510.

Figure 6:
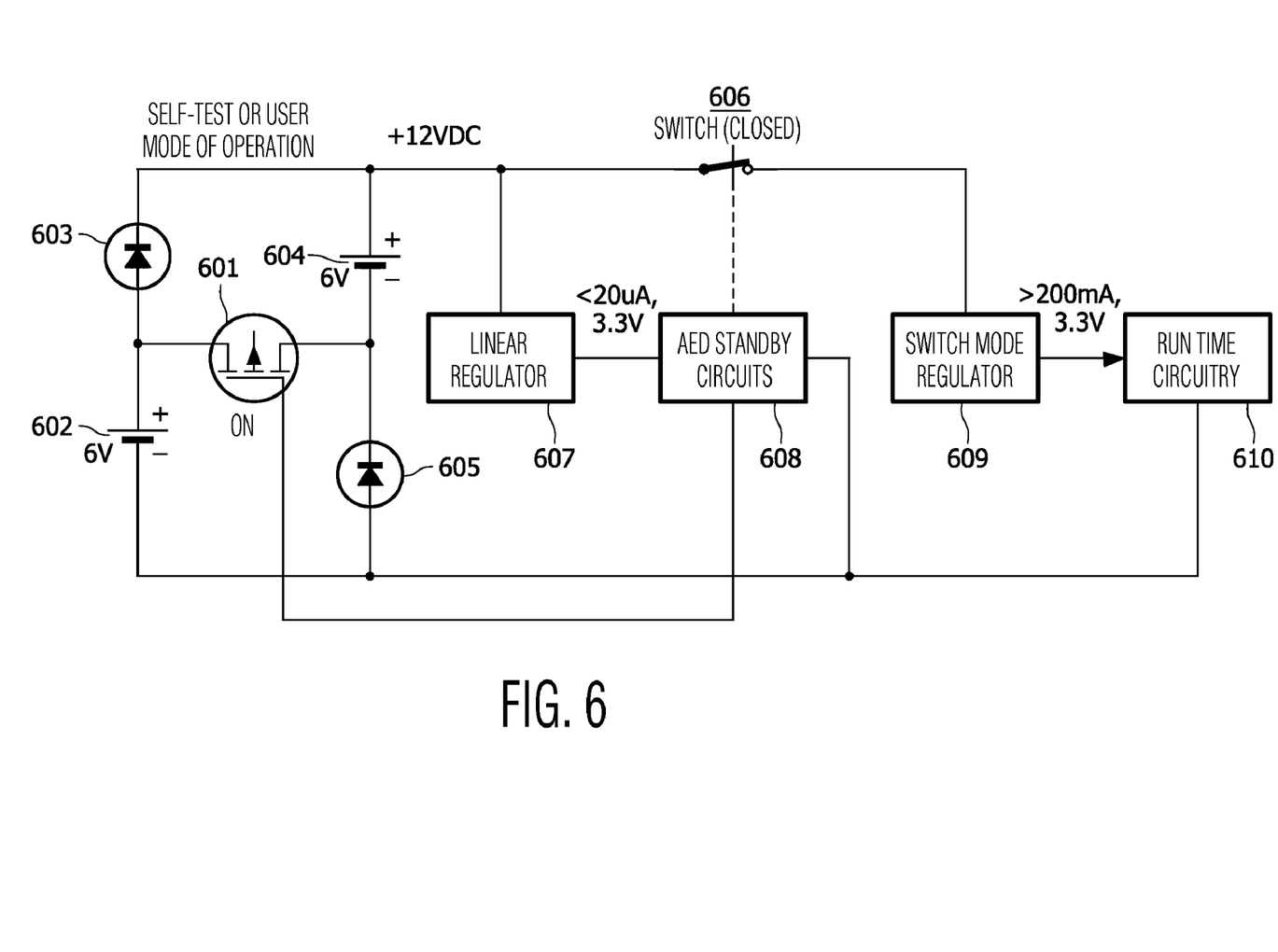
FIG. 6 shows the circuit when the AED is operating in run-time mode.

FIG. 6 shows the previous circuit when the AED is operating in run-time mode. Switch 601 is now closed and batteries 602 and 604 operate in series generating optimally 12V. Switch 506 is now closed supplying power to the Switch Mode Regulator 509 which operates efficiently at the higher voltage. Power is transferred through the Switch Mode Regulator 509 to the Run-time Circuitry 610. The embodiment of using at least two batteries, connected in parallel when the AED operates in stand-by mode, and connected in series when the AED operates in run-time mode, has the effect of providing two separate voltage sources which can each be matched to the voltage requirements of each mode of operation.

The invention can be used wherever a battery or other independent, non-mains voltage source is used within a defibrillator. This may be when a normal, mains-operated defibrillator is disconnected from mains voltage and required to operate without the advantage of mains power, but may also be in a dedicated, battery powered defibrillator. Thus it can be utilized in external defibrillators carried by paramedic personnel outside hospital environments. The invention serves to extend battery life during long periods of non-use and, as has been described, is particularly advantageous when used within an automatic external defibrillator. In this case advantageous results are obtained when there are only two batteries or battery compositions. This allows two different voltages to be provided by the automatic external defibrillator while keeping the number of components to a reasonable level concomitant with providing a small, lightweight and therefore easily transportable automatic external defibrillator.

An embodiment of the present invention also finds utility in an environment when different systems, such as different AEDs, require different supply voltages. In such case a switchable battery pack of the present invention can be connected differently when used in the different AEDs. For instance, using the previous example of a battery pack consisting of a plurality of 4 volt batteries, the battery pack could be installed in one AED to provide a 12V source and an 8V source. When the same battery pack is installed in another AED it could provide a 12V source and a 4V source, the difference arising by different battery connection circuitry in the two different units. It may be seen that such an embodiment provides an advantage to a manufacturer of AEDs with different supply voltage requirements, as only one battery pack needs to be stocked and supplied to users of both types of AEDs, providing efficiencies in volume manufacturing and inventory control.

The invention claimed is:

1. A defibrillator, equipped with a battery power source having a plurality of batteries for the purposes of operation in a first stand-by mode in which low voltage circuit are powered, and in a second run-time mode in which a high power capacitor is charged, characterized in that:

batteries are arranged to be connected in parallel to each other when the defibrillator is operating in the first mode so that all of the batteries are drawn down at the same rate in the first mode, and that the batteries are arranged to be connected in series with each other when the defibrillator is operating in second mode so that all of the batteries are drawn down at the same rate in the second mode, wherein the batteries reach the same minimum voltage at the same time regardless of the operating mode used.

2. A defibrillator as claimed in claim 1, wherein the batteries are switchable between a first, low voltage arrangement in the first mode and a second, high voltage arrangement in the second mode.

3. A defibrillator as claimed in claim 2, wherein the defibrillator further contains regulators to regulate the voltage applied in each mode.

4. A defibrillator as claimed in claim 2, further comprising a linear regulator which acts to regulate the output from the battery power source when operating in the first mode.

5. A defibrillator as claimed in claim 2, further comprising a switching regulator which acts to regulate the output from the battery power source in the second mode.

6. A defibrillator as claimed in claim 1, wherein the first mode and the second mode utilize different voltages.

7. A defibrillator as claimed in claim 1, wherein the first mode is a stand by mode in which the voltage requirement of the defibrillator is lower than in the second mode.

8. A defibrillator as claimed in claim 7, wherein while in stand-by mode the defibrillator draws less than 1 milliamp, or draws less than 100 microamps, or draws less than 50 microamps, or draws less than 25 microamps.

9. A defibrillator as claimed in claim 1, wherein the defibrillator is an automatic external defibrillator.

10. A defibrillator including circuitry with a plurality of different voltage requirements and arranged to operate in any one of a first stand-by mode in which low voltage circuits are powered and a second operating mode in which a high power capacitor is charged, comprising a battery power source comprising at least two batteries, coupled to the defibrillator circuitry, the batteries being arranged to be coupled in parallel so as to be drawn down at the same rate when the defibrillator is operating in the first mode, and the batteries being arranged to be coupled in series so as to be drawn down at the same rate when the defibrillator is operating in the second mode, whereby the battery live is extended.

11. A defibrillator as claimed in claim 10, further comprising a switching device operable to selectively connect the batteries in series or in parallel.

12. A defibrillator as claimed in claim 11, wherein the switching device comprises a mechanical switch.

13. A defibrillator as claimed in claim 11, wherein the switching device comprises a semiconductor switching device.

* * * * *